(12) United States Patent
Hatakoshi

(10) Patent No.: US 6,221,890 B1
(45) Date of Patent: Apr. 24, 2001

(54) ACARICIDAL COMPOSITIONS

(75) Inventor: Makoto Hatakoshi, Toyonaka (JP)

(73) Assignee: Sumitomo Chemical Company Limited, Osaka (JP)

( * ) Notice: Subject to any disclaimer, the term of this patent is extended or adjusted under 35 U.S.C. 154(b) by 0 days.

(21) Appl. No.: 09/422,566

(22) Filed: Oct. 21, 1999

(51) Int. Cl.⁷ .................. A01N 43/76; A01N 37/12; A01N 37/44
(52) U.S. Cl. ................ 514/374; 514/535; 514/537
(58) Field of Search .................... 514/535, 537, 514/374

(56) References Cited

FOREIGN PATENT DOCUMENTS

| 57-156407 | 9/1982 | (JP) . |
| 8-319202 | 12/1996 | (JP) . |
| WO 93/22297 | 11/1993 | (WO) . |

*Primary Examiner*—Allen J. Robinson
(74) *Attorney, Agent, or Firm*—Sughrue, Mion, Zinn, Macpeak & Seas, PLLC

(57) ABSTRACT

Provided are novel acaricidal compositions which posses a synergistic acaricidal activity. As such, the acaricidal compositions of the instant invention generally contain 2-methoxycarbonyl-4-chlorotrifluoromethanesulfonanilide and 2-(2,6-difluorophenyl)-4-(2-ethoxy-4-tert-butylphenyl)-2-oxazoline together as active ingredients. Such acaricidal compositions may be utilized in methods of controlling acarina.

7 Claims, No Drawings

ACARICIDAL COMPOSITIONS

BACKGROUND OF THE INVENTION

1. Field of the Invention

The instant invention relates to acaricidal compositions and methods of controlling acarina.

2. Description of Related Art

Japanese laid open patent Hei 8-319202 describes trifluoromethanesulfonanilide compounds as possessing an acaricidal activity.

WO 93/22297 describes oxazoline compounds as possessing an acaricidal activity.

In cases of using the trifluoromethanesulfonanilide compounds or the oxazoline compounds as a singular active ingredient in a composition for controlling acarina, a large amount of the active ingredient is needed to effectively control acarina.

SUMMARY OF THE INVENTION

The instant invention provides superior acaricidal compositions which can be utilized to effectively control acarina. As such, the acaricidal compositions of the instant invention possess a synergistic acaricidal activity which is unexpectedly superior to that provided from individually utilizing a trifluoromethanesulfonanilide compound or an oxazoline compound as a sole active ingredient in a composition.

The instant invention fulfills such acaricidal properties by providing acaricidal compositions which comprise 2-methylcarbonyl-4-chlorotrifluoromethanesulfonanilide and 2-(2,6-difluorophenyl)-4-(2-ethoxy-4-tert-butylphenyl)-2-oxazoline together as active ingredients therein. Additionally, the instant invention provides methods of controlling acarina which comprise applying 2-methoxycarbonyl-4-chlorotrifluoromethanesulfonanilide and 2-(2,6-difluorophenyl)-4-(2-ethoxy-4-tert-butylphenyl)-2-oxazoline to acarina or a locus of where the acarina inhabits.

DETAILED DESCRIPTION OF THE INVENTION

An acaricidal composition of the instant invention comprises 2-methoxycarbonyl-4-chlorotrifluoromethanesulfonanilide and 2-(2,6-difluorophenyl)-4-(2-ethoxy-4-tert-butylphenyl)-2-oxazoline together as active ingredients. Preferably the weight to weight ratio of 2-methoxycarbonyl-4-chlorotrifluoromethanesulfonanilide to 2-(2,6-difluorophenyl)-4-(2-ethoxy-4-tert-butylphenyl)-2-oxazoline in the acaricidal composition is from about 1:0.1 to 1:10. In addition, the total amount of the active ingredients in said acaricidal composition is generally from about 0.02 to 99% by weight, wherein said percentage by weight is based on the total weight of the provided acaricidal composition. For example, the acaricidal compositions can comprise 2-methoxycarbonyl-4-chlorotrifluoromethanesulfonanilide in an amount of from about 0.01 to 90% by weight and 2-(2,6-difluorophenyl)-4-(2-ethoxy-4-tert-butylphenyl)-2-oxazoline in an amount of from about 0.01 to 90% by weight, wherein said percentages by weight are based on the total weight of the provided acaricidal composition.

The acaricidal compositions of the instant invention are usually formulated into sheets, tablets, fumigants, granules, oily solutions, emulsifiable concentrates, dusts, aerosols, and the like. Such formulations are preferably applied to the acarina or are utilized in locations in which a control of acarina is desired, in order to control acarina. Illustrative and non-limiting examples of locations of where said formulations may be utilized to control acarina include indoor floors, a habitat of an acarina, carpets, sofas, and the like.

The formulations of the inventive acaricidal compositions can treat such locations so that an acaricidally effective amount of the active ingredients is utilized to treat such locations. Such an acaricidally effective amount of the active ingredients may vary, but the formulations preferably utilize from about 0.01 to 2 g of the active ingredients per 1 $m^2$ of a locus or from about 0.001 to 2 g of the active ingredients per 1 $m^3$ of space to effectively control acarina.

It is preferable for the sheet formulations of the acaricidal compositions to have 2-methoxycarbonyl-4-chlorotrifluoromethanesulfonanilide and 2-(2,6-difluorophenyl)-4-(2-ethoxy-4-tert-butylphenyl)-2-oxazoline supported on a sheet. In order to produce the sheet formulations of the inventive acaricidal compositions, the active ingredients can be spread on a sheet or a sheet can be soaked in a solution or suspension containing the active ingredients to produce the sheet formulation. Further, the acaricidal compositions can also be formed to a sheet formulation by forming sheet material which already contain the active ingredients into said sheet formulations. Furthermore, a solvent which comprises the active ingredients may also be utilized to support said active ingredients on a sheet. When adding the active ingredients to the sheet material, the active ingredients may be kneaded into said sheet material. In addition, the active ingredients in the sheet formulations can be distributed therein so that the concentration of said active ingredients is from about 0.01 to 2 g per 1 $m^2$ of the sheet formulation.

Such solvents which are utilized to contain the active ingredients and produce the sheet formulations are preferably organic solvents, with examples of the organic solvents including ketone solvents such as acetone, alcohol solvents such as methanol, ester solvents such as ethyl acetate, halogenated aliphatic hydrocarbon solvents such as dichloromethane, aromatic hydrocarbons such as benzene and toluene, aliphatic hydrocarbons such as hexane and kerosene, and the like, but are not limited thereto.

The sheets which are utilized to formulate the sheet formulations of the inventive acaricidal compositions may have the dimensions of a generally flat shape, in which the thickness thereof may be from about 0.01 to 10 mm. In such cases, a sheet material which is utilized to produce the sheet formulations can comprise a synthetic resin film such as paper, polyolefin, polyester or polyvinylchloride, a woven textile of natural-occurring fibers such as jute, silk, wool or cotton, or the like.

The tablet formulations of the acaricidal compositions additionally comprise a porous carrier. Porous carriers which can be in the tablet formulations should preferably be able to preserve the active ingredients therein and also allow the active ingredients to release therefrom at an appropriate temperature. Illustrative and non-limiting examples of the porous carriers include cotton linters, ceramic boards, non-woven fabric, thick paper, and the like.

When utilizing the tablet formulations to control acarina, it is preferable to heat the tablet formulations to a temperature which allow the active ingredients therein to vaporize and disperse the active ingredients into the surrounding spaces thereof. Such temperatures may vary, but a temperature of from about 100 to 300° C. is preferable to vaporize the active ingredients in the tablet formulations. A commercially available mosquito mat heater may be utilized to heat the tablet formulation, if so desired. The size of the tablet formulations is typically from about 10 mm×20 mm×1 mm to 35 mm×50 mm×4 mm, preferably about 22 mm×35 mm×2.8 mm, and that may be utilized in commercial heater for controlling mosquitoes.

The fumigant formulations of the acaricidal compositions can additionally comprise a foaming agent therein. The foaming agents in the fumigant formulations are preferably organic and can provide a gas such as nitrogen when activated or heat decomposed. Illustrative and non-limiting examples of organic foaming agents which can be utilized in a combustion or non-combustion type fumigant formulation include azodicarbonamide, azobisisobutyronitrile, 2-(carbamoylazo)isobutyronitrile, dinitroisopentamethylenetetramine, p,p'-oxybis (benzenesulfonylhydrazide and the like.

Said combustion type fumigant formulations of the acaricidal compositions are generally produced by mixing 2-methoxycarbonyl-4-trifluoromethanesulfonanilide, 2-(2, 6-difluorophenyl)-4-(2-ethoxy-4-tert-butylphenyl)-2-oxazoline, the foaming agent and a combusting agent. Preferably, in order to produce the combustion type fumigant formulations, water is additionally mixed into the mixture, the achieved mixture is kneaded into an useful form such as a granule, and the mixture is dried. More preferably, the combustion fumigant formulations also have a combustion auxiliary mixed therein. Exemplarily of combustion auxiliaries which may be utilized in the combustion fumigant formulations include an oxygen supplying agent, a heat controlling agent, an auxiliary which decomposes the oxygen supplying agents therein, an inorganic carrier and the like, but is not limited thereto.

It generally is a function of the combusting agents in the combustion type fumigant formulations to provide the main charge in the combustion reaction therein. Illustrative and non-limiting examples of the combustion agents include saccharides, starches, and the like.

The oxygen supplying agents are provided in the combustion type fumigant formulations to generally help provide oxygen to a combustion reaction therein. Such oxygen supplying agents preferably undergo pyrolysis to supply the oxygen to the combustion reaction. Illustrative and non-limiting examples of the oxygen providing agents include potassium perchlorate, potassium nitrate, potassium chlorate and the like.

The heat controlling agents in the combustion type formulations are preferably utilized to control the heat in the combustion reaction therein. For example, a heat controlling agent may be utilized therein to lower the heat of the combustion reaction. Illustrative and non-limiting examples of heat controlling agents which can be utilized in the combustion type fumigant formulations include guanidine nitrate, nitroguanidine, dicyandiamide, guanylphosphate urea, guanidine sulfaminate, and the like.

The auxiliaries which decompose the oxygen supplying agents in the combustion type fumigant formulations generally assist in the pyrolysis of a particular oxygen supplying agent therein, so that the oxygen provided to the combustion reaction therein is controlled. Illustrative and non-limiting examples of the auxiliaries which decompose the oxygen supplying agents include potassium chloride, sodium chloride, iron (II, III) oxide, copper oxide, chromium oxide, iron oxide, activated carbon, and the like.

Illustrative and non-limiting examples of inorganic carriers which are utilized in the combustion type fumigant formulations include perlite, diatomaceous earth, talc, clay, and the like.

The non-combustion type fumigant formulations of the acaricidal compositions are generally produced by mixing the foaming agent, the 2-methoxycarbonyl-4-chlorotrifluoromethanesulfonanilide and 2-(2,6-difluorophenyl)-4-(2-ethoxy-4-tert-butylphenyl)-2-oxazoline together and adding a non-combustion heating agent thereto. Preferably, in order to produce the non-combustion type fumigant formulation, the non-combustion fumigant formulations additionally have water mixed into said mixture of the active ingredients and foaming agent, the achieved mixture kneaded into an useful form, and the mixture dried. More preferably, the non-combustion fumigant formulations also have a binder and flocculant mixed therein and have the kneaded mixture formed as a granule.

The fumigant formulations of the inventive acaricidal compositions can utilize a combustion reaction or a non-combustion reaction to control acarina.

The combustion type fumigant formulations of the inventive acaricidal compositions may be utilized to control acarina by loading said formulation into a container such as a paper tube, adding an igniting agent such as thermit thereto, and then igniting the formulation, so that said formulation can fumigate the active ingredients.

Illustrative and non-limiting examples of binders which can be utilized in the non-combustion fumigant formulations include polyvinyl alcohol, carboxymethyl cellulose, starch, and the like.

The flocculants in the non-combustion fumigant formulation are preferably materials which can produce flocs. As such, the flocculant in the non-combustion fumigant formulations may be zinc oxide, but is not limited thereto.

The non-combustion fumigant formulations of the inventive acaricidal compositions are typically utilized to control acarina by activating the non-combustion heating agent therein and allowing the non-combustion fumigant formulation to fumigate the active ingredients. For example, in a container which is partitioned into two sections, the granules containing said active ingredients may be placed into one of the sections of the container and the non-combustion heating agent may be placed into the other section of said container, and the non-combustion heating agent may then be activated, in order to activate the non-combustion fumigant formulation and control acarina therewith. The gas produced from the foaming agent in the non-combustion fumigant formulation usually allows the active ingredients to disperse therefrom to the surrounding space of said formulation. A description of utilizing a non-combustion heating formulation to control pests is provided in Japanese laid open patent sho 59-49201.

The non-combustion heating agent can be utilized in the non-combustion fumigant formulations of the acaricidal compositions to provide an effective amount of heat therein, when activated. The effective amount of heat provided by the non-combustion heating agent therein typically can decompose the foaming agent therein, so that the foaming agent can provide a gas. For example, a heating agent which produces a temperature of more than about 300° C., when activated, may be utilized in the non-combustion fumigant formulation, if so desired. In this regard, the non-combustion heating agent may be calcium oxide. When calcium oxide is utilized as the non combustion heating agent in the non-combustion fumigant formulation, water is typically added to the calcium oxide therein, so that the calcium oxide is activated.

In formulating the inventive acaricidal compositions as said oily solutions, emulsifiable concentrates, dusts, granules, aerosols and the like, a liquid or solid carrier or propellant is typically present in the formulations. The carriers are preferably utilized in the formulations to vehicle or assist the active ingredients to arrive at sites, or which to allow easier storage, transport, or handling of the active ingredients.

Illustrative and non-limiting examples of liquid carriers which can be utilized in the acaricidal compositions include hydrocarbons such as toluene, xylene, methylnaphthalene, phenylxylylethane, kerosene, hexane and cyclohexane, ethers such as diethyl ether, ethylene glycol dimethyl ether, tetrahydrofuran, and dioxane, ketones such as acetone, methyl ethyl ketone, methyl isobutyl ketone, cyclohexanone and isophorone, alcohols such as methanol, ethanol, isopropyl alcohol, hexanol and ethyleneglycol, amides such as N,N-dimethylformamide and N,N-dimethylacetamide, and the like.

Illustrative and non-limiting examples of solid carriers which can be utilized in the acaricidal compositions include talc, bentonite, clay, caolin, diatomaceous earth, silica, vermiculite, perlite, and the like.

Illustrative and non-limiting examples of propellants which can be utilized in the acaricidal compositions include nitrogen, carbonate gas, dimethyl ether, LPG, and the like.

The instant inventive compositions can also be additionally mixed or used in combination with synergists, germicides, fungicides, other insecticidally or acaricidally active compounds such as d-phenothrin, empenthrin and metoxadiazone, or the like, to control acarina.

The acaricidal compositions of the instant invention can control acarina which typically inhabit an indoor area. Illustrative and non-limiting examples of acarina which can be controlled by using the inventive acaricidal compositions include Dermanyssidae such as American house dust mite (*Dermatophagoides farinae*) and *Dermatophagoides pternonyssinus*, Acaridae such as *Lardoglyphus konoi*, mold or copra or forage mite (*Tyrophagus putrescentiae*) and brown legged grain mite (*Aleuroglyphus ovatus*), Glycyphagidae such as *Glycyphagus privatus, Glycyphagus domesticus*, groceries mite (*Glycyphagus destuctor*), and chortoglyphus spp., Cheyletidae such as *Chelacaropsis moorei, Chelacaropsis malaccensis, Cheyletus fortis, Cheyletus eruditus* and *Chelatomorpha lepidoterorum*, Macronyssidae such as *Ornithonyssus bacoti, Ornithonyssus sylviarum, Dermanyssus gallinae* and *Dermanyssus hirundinis*, Haplochthonius simplex, Pyemotidae, and Sarcoptidae, and the like. In addition, the acaricidal compositions can also control other pests, with examples of said other pests including fleas (Pulicidae) such as cat flea (*Ctenocephalides felis*) and dog flea (*Ctenocephalides canis*), cockroaches (Blattidae) such as German cockroach (*Blattella germanica*) and smokybrown cockroach (*Periplaneta fuliginosa*), booklice, barklice or psocids (Psocoptera) such as *Liposcelis bostrychophilus* and *Liposcelis entomophilus*, ants (Formicidae) such as little red ant (*Monomorium pharaonis*), Cimicidae such as *Cinnex lectularius*, and the like.

It should be noted, when utilizing 2-methoxycarbonyl-4-chlorotrifluoromethanesulfonanilide and 2-(2,6-difluorophenyl)-4-(2-ethoxy-4-tert-butylphenyl)-2-oxazoline together to control acarina, that said active ingredients can be applied to a locus as a mixture, applied in a sequential manner in which one of the active ingredients is applied to a locus and then the second active ingredient is applied to said locus, or applied in a separate but simultaneous manner in which each of the active ingredients are in separate compositions and are applied to a locus simultaneously.

EXAMPLES

Formulation Example 1

A mixture consisting of 5 parts by weight of 2-methoxycarbonyl-4-chlorotrifluoromethanesulfonanilide, 5 parts by weight of 2-(2,6-difluorophenyl)-4-(2-ethoxy-4-tert-butylphenyl)-2-oxazoline, 0.5 parts by weight of zinc oxide and 2 parts by weight of α-starch is added to azodicarbonamide to amount to 100 parts by weight. Water is added to the achieved mixture and the mixture is kneaded. The kneaded mixture is formed into a granule form by using an extrusion machine and is then allowed to dry, in order to obtain a combustion type fumigant formulation of the instant invention.

Formulation Example 2

A mixture consisting of 0.75 g of 2-methoxycarbonyl-4-chlorotrifluoromethanesulfonanilide, 0.75 g of 2-(2,6-difluorophenyl)-4-(2-ethoxy-4-tert-butylphenyl)-2-oxazoline, 2.5 g of azodicarbonamide, 1.5 g nitrocellulose, 0.4 g of dibutyl phthalate, 0.54 g of zinc oxide, 2.56 g of perlite, and 1.0 g of polyvinyl alcohol is formed. One of the inventive combustion type fumigant formulations is then produced by adding water to the achieved mixture, kneading the mixture, forming the mixture into a granule by use of a extrusion machine, and drying the mixture.

Formulation Example 3

An acetone solution containing 0.5 g of 2-methoxycarbonyl-4-chlorotrifluoromethanesulfonanilide and 0.5 g of 2-(2,6-difluorophenyl)-4-(2-ethoxy-4-tert-butylphenyl)-2-oxazoline is spread onto a porous ceramic material having a width of 4.2 cm, a depth of 4.2 cm, a thickness of 1.2 cm and a pore diameter of 0.3 cm, as well as 102 pores therein, wherein said percentages by weight are based on the total weight of the mixture. The achieved porous ceramic material is allowed to dry, in order to achieve a tablet formulation of the instant invention.

Formulation Example 4

Each of 2-methoxycarbonyl-4-chlorotrifluoromethanesulfonanilide and 2-(2,6-difluorophenyl)-4-(2-ethoxy-4-tert-butylphenyl)-2-oxazoline is diluted in acetone, respectively, and is spread onto a kraft paper, so that the concentration of 2-methoxycarbonyl-4-chlorotrifluoromethanesulfonanilide therein is 0.8 g per 1 $m^2$ of said paper and the concentration of 2-(2,6-difluorophenyl)-4-(2-ethoxy-4-tert-butylphenyl)-2-oxazoline therein is 0.3 g per 1 $m^2$ of said paper. The kraft paper is allowed to absorb 2-methoxycarbonyl-4-chlorotrifluoromethanesulfonanilide and 2-(2,6-difluorophenyl)-4-(2-ethoxy-4-tert-butylphenyl)-2-oxazoline, and the achieved paper is then allowed to dry to achieve a sheet formulation of the instant invention.

Formulation Example 5

One-third (0.33) part by weight of 2-methoxycarbonyl-4-chlorotrifluoromethanesulfonanilide and 0.33 parts by weight of 2-(2,6-difluorophenyl)-4-(2-ethoxy-4-tert-butylphenyl)-2-oxazoline is placed in an aerosol container, and Isopar M (provided by Exxon Chemical Company) is added thereto to amount to 25 parts by weight. After attaching an aerosol valve to the aerosol container, 75 parts by weight of dimethyl ether is loaded into the container and a total release aerosol actuator is then added onto the container, in order to achieve 25 g of an aerosol formulation of the instant invention. Said percentages by weight are based on the total weight of the aerosol formulation.

Test Example 1

In order to produce 3 types of acaricidal compositions, 2-methoxycarbonyl-4-chlorotrifluoromethanesulfonanilide and 2-(2,6-difluorophenyl)-4-(2-ethoxy-4-tert-butylphenyl)-2-oxazoline and a mixture thereof were diluted, respectively, with isopropyl alcohol and water, so that the concentration of each of said compounds therein was 0.1% weight by volume.

American house dust mite eggs (*Dermatophagoides farinae*), which were oviposited less than 24 hours previously, were placed onto filter papers having a 3.8 cm diameter. Three-fifths milliliters (0.6 mL) of each of the achieved acaricidal compositions were deposited, repectively, onto said filter papers. The eggs were then allowed to be exposed to the compositions for a time period of 1 minute. Subsequently, the eggs were transferred to untreated filter papers, and were preserved at a temperature of 25° C. and humidity of 65% for 10 days. The eggs were then examined to determine the number of hatched eggs thereof and the results are given below in Table 1.

TABLE 1

| Tested Compounds | Concentration (wt/v %) | No. of tested eggs | No. of hatched eggs |
|---|---|---|---|
| 2-methoxycarbonyl-4-chlorotrifluoromethanesulfonanilide | 0.1 | 15 | 14 |
| 2-(2,6-difluorophenyl)-4-(2-ethoxy-4-tert-butylphenyl)-2-oxazoline | 0.1 | 16 | 5 |
| 2-methoxycarbonyl-4-chlorotrifluoromethanesulfonanilide and 2-(2,6-difluorophenyl)-4-(2-ethoxy-4-tert-butylphenyl)-2-oxazoline | 0.1 + 0.1 | 14 | 0 |

Test Example 2

2-Methoxycarbonyl-4-chlorotrifluoromethanesulfonanilide and 2-(2,6-difluorophenyl)-4-(2-ethoxy-4-tert-butylphenyl)-2-oxazoline and a mixture thereof were diluted, respectively, with isopropyl alcohol and water. The concentration of 2-methoxycarbonyl-4-chlorotrifluoromethanesulfonanilide in an achieved composition was 0.5% weight by volume. The concentration of 2-(2,6-difluorophenyl)-4-(2-ethoxy-4-tert-butylphenyl)-2-oxazolinc in an achieved composition was 0.1% weight by volume. The concentration of said mixture thereof was at a concentration in which 2-methoxycarbonyl-4-chlorotrifluoromethanesulfonanilide was at 0.5% weight by volume and 2-methoxycarbonyl-4-chlorotrifluoromethanesulfonanilide was at 0.1% weight by volume.

Adult American house dust mites (*Dermatophagoides farinae*) and eggs thereof which were oviposited less than 24 hours previously, were placed onto filter papers having a 3.8 cm diameter. Three-fifths milliliters (0.6mL) of each of the achieved acaricidal compositions were deposited, repectively, onto said filter papers. The eggs and adult mites were then allowed to be exposed to the compositions for a time period of 1 minute. Subsequently, the eggs and adult mites were transferred to untreated filter papers, and were preserved at a temperature of 25° C. and humidity of 65% for 10 days. The eggs and adult mites were then examined to determine the number of surviving larvae, nymphs, and adult mites. The results are given below in Table 2.

TABLE 2

| Tested Compounds | Concentration (wt/v %) | No. before application: eggs | No. before application: adults | Surviving mites 10 days thereafter |
|---|---|---|---|---|
| 2-methoxycarbonyl-4-chlorotrifluoromethane-sulfonanilide | 0.5 | 18 | 23 | 18 |
| 2-(2,6-difluorophenyl)-4-(2-ethoxy-4-tert-butylphenyl)-2-oxazoline | 0.1 | 19 | 21 | 14 |
| 2-methoxycarbonyl-4-chlorotrifluoromethane-sulfonanilide and 2-(2,6-difluorophenyl)-4-(2-ethoxy-4-tert-butylphenyl)-2-oxazoline | 0.5 + 0.1 | 17 | 21 | 5 |

The above results evidence that the compositions of the instant invention provide unexpected and synergistic acaricidal activity, and that the removal of one of the active ingredients therefrom would not result in such superior acaricidal activity.

Each of the publications and patents described in the instant specification are incorporated herein by reference in their entirety.

What is claimed is:

1. An acaricidal composition comprising as active ingredients therein: synergistic acaricidally effective amounts of (i) 2-methoxycarbonyl-4-chlorotrifluoromethanesulfonanilide and (ii) 2-(2,6-difluorophenyl)-4-(2-ethoxy-4-tert-butylphenyl)-2-oxazoline.

2. The acaricidal composition of claim 1, wherein a weight to weight ratio of said 2-methoxycarbonyl-4-chlorotrifluoromethanesulfonanilide to said 2-(2,6-difluorophenyl)-4-(2-ethoxy-4-tert-butylphenyl)-2-oxazoline in said acaricidal composition is from about 1:0.1 to 1:10.

3. The acaricidal composition according to claim 1, wherein the total amount of 2-methoxycarbonyl-4-chlorotrifluoromethanesulfonanilide and 2-(2,6difluorophenyl)-4-(2-ethoxy-4-tert-butylphenyl)-2-oxazoline is from about 0.02 to 99% by weight, based on the total weight of the provided acaricidal composition.

4. A method of controlling acarina, comprising applying a synergistic acaricidally effective amount of 2-methoxycarbonyl-4-chlorotrifluoromethanesulfonanilide and 2-(2,6-difluorophenyl)-4-(2-ethoxy-4-tert-butylphenyl)-2-oxazoline, to a locus of where a control of acarina is desired.

5. The method according to claim 4, wherein the weight to weight ratio of 2-methoxycarbonyl-4-chlorotrifluoromethanesulfonanilide to 2-(2,6-difluorophenyl)-4-(2-ethoxy-4-tert-butylphenyl)-2-oxazoline is from about 1:0.1 to 1:10.

6. The method of controlling acarina according to claim 4, wherein said locus of where a control of acarina is desired is an indoor floor, habitat of an acarina, carpet or sofa.

7. The method of controlling acarina according to claim 4, wherein the acarina is a Dermanyssidae, Acaridae, Glycyphagidae, Cheyletidae, Macronussidae, *Haplochthonius simplex*, Pyemotidae, or Sacroptidae.

* * * * *